(12) United States Patent
Daher et al.

(10) Patent No.: US 10,888,679 B2
(45) Date of Patent: *Jan. 12, 2021

(54) ENDOBRONCHIAL TUBE WITH INTEGRATED IMAGE SENSOR

(71) Applicant: AMBU A/S, Ballerup (DK)

(72) Inventors: Elias Daher, Bielefeld (DE); Matthias Benedikt Schuh, Obersuessbach (DE)

(73) Assignee: AMBU A/S, Ballerup (DK)

( * ) Notice: Subject to any disclaimer, the term of this patent is extended or adjusted under 35 U.S.C. 154(b) by 4 days.

This patent is subject to a terminal disclaimer.

(21) Appl. No.: 16/369,803

(22) Filed: Mar. 29, 2019

(65) Prior Publication Data

US 2019/0224433 A1    Jul. 25, 2019

Related U.S. Application Data

(63) Continuation of application No. 14/967,048, filed on Dec. 11, 2015, now Pat. No. 10,245,402, which is a
(Continued)

(51) Int. Cl.
*A61B 1/07* (2006.01)
*A61M 16/04* (2006.01)
(Continued)

(52) U.S. Cl.
CPC ..... *A61M 16/0463* (2013.01); *A61B 1/00018* (2013.01); *A61B 1/00082* (2013.01);
(Continued)

(58) Field of Classification Search
CPC .. A61B 1/01; A61B 1/015; A61B 1/07; A61B 1/00009; A61B 1/00147;
(Continued)

(56) References Cited

U.S. PATENT DOCUMENTS 543,616 A    7/1895  Dow
1,246,339 A  11/1917 Smit
(Continued)

FOREIGN PATENT DOCUMENTS

CN    201862108 U    6/2011
DE    4132687 A1     4/1993
(Continued)

*Primary Examiner* — Timothy J Neal
*Assistant Examiner* — William B Chou
(74) *Attorney, Agent, or Firm* — Faegre Drinker Biddle & Reath

(57) ABSTRACT

An endobronchial tube comprising at least two lumens of different lengths for selectively associating with a patient about at least two locations relative to the Tracheal Carina. said tube comprising: a first lumen having an open distal end that associates proximally to the Carina within the Trachea, with a first inflatable cuff; a second lumen having an open distal end that extends distally, past the Carina and associates within one of the Left Bronchial branch and Right Bronchial branch with a second inflatable cuff; a dedicated image sensor lumen spanning the length of said first lumen, the dedicated image sensor lumen comprising an image sensor and illumination source disposed adjacent to the distal end of said first lumen, and configured to provide an image of the Tracheal bifurcation of the Tracheal Carina, the openings of the Left Bronchial branch, and the opening Right Bronchial branch; and at least one dedicated cleaning lumen disposed parallel with said dedicated image sensor lumen along the length of said endobronchial tube and wherein said cleaning lumen is configured to forms a cleaning nozzle at the distal end, wherein said cleaning nozzle is directed toward said image sensor lumen at its distal end.

13 Claims, 9 Drawing Sheets

Related U.S. Application Data continuation of application No. 13/819,743, filed as application No. PCT/IB2012/052077 on Apr. 26, 2012, now abandoned.

(60) Provisional application No. 61/506,210, filed on Jul. 11, 2011.

(51) Int. Cl.

| | | |
|---|---|---|
| *A61M 16/08* | (2006.01) | |
| *A61B 1/00* | (2006.01) | |
| *A61B 1/12* | (2006.01) | |
| *A61B 1/267* | (2006.01) | |
| *A61B 1/012* | (2006.01) | |
| *A61B 1/05* | (2006.01) | |
| *A61B 1/06* | (2006.01) | |
| *A61B 1/313* | (2006.01) | |
| *A61M 16/00* | (2006.01) | |
| *A61M 16/10* | (2006.01) | |
| *A61B 1/015* | (2006.01) | |
| *A61M 15/00* | (2006.01) | |

(52) U.S. Cl.
CPC ...... *A61B 1/00091* (2013.01); *A61B 1/00094* (2013.01); *A61B 1/00124* (2013.01); *A61B 1/012* (2013.01); *A61B 1/015* (2013.01); *A61B 1/05* (2013.01); *A61B 1/051* (2013.01); *A61B 1/0676* (2013.01); *A61B 1/0684* (2013.01); *A61B 1/07* (2013.01); *A61B 1/12* (2013.01); *A61B 1/126* (2013.01); *A61B 1/2676* (2013.01); *A61B 1/313* (2013.01); *A61M 16/0057* (2013.01); *A61M 16/04* (2013.01); *A61M 16/0404* (2014.02); *A61M 16/0434* (2013.01); *A61M 16/0459* (2014.02); *A61M 16/0461* (2013.01); *A61M 16/0465* (2013.01); *A61M 16/0486* (2014.02); *A61M 16/0488* (2013.01); *A61M 16/0833* (2014.02); *A61M 16/104* (2013.01); *A61M 15/00* (2013.01)

(58) Field of Classification Search
CPC ............ A61B 1/00154; A61B 1/00131; A61B 1/00135; A61B 1/00066; A61B 1/00071; A61B 1/0008; A61B 1/00082; A61B 1/00091; A61B 1/00094
See application file for complete search history.

(56) References Cited

U.S. PATENT DOCUMENTS

| | | |
|---|---|---|
| 2,797,683 A | 7/1957 | Aiken |
| 3,350,553 A | 10/1967 | Cline |
| 3,539,794 A | 11/1970 | Rauhut et al. |
| 3,576,987 A | 5/1971 | Voight et al. |
| 3,716,047 A | 2/1973 | Moore et al. |
| 3,729,425 A | 4/1973 | Heller et al. |
| 3,776,222 A | 12/1973 | Smiddy |
| 3,808,414 A | 4/1974 | Roberts |
| 3,893,938 A | 7/1975 | Rauhut |
| 4,150,676 A | 4/1979 | Jackson |
| 4,253,447 A | 3/1981 | Moore et al. |
| 4,383,534 A | 5/1983 | Peters |
| 4,437,458 A | 3/1984 | Upsher |
| 4,509,507 A | 4/1985 | Yabe |
| 4,567,882 A | 2/1986 | Heller |
| 4,602,281 A | 7/1986 | Nagasaki et al. |
| 4,616,631 A | 10/1986 | Takahashi |
| 4,635,166 A | 1/1987 | Cameron |
| 4,643,170 A | 2/1987 | Miyazaki et al. |
| 4,742,819 A | 5/1988 | George |
| 4,759,346 A | 7/1988 | Nakajima |
| 4,813,431 A | 3/1989 | Brown |
| 4,814,949 A | 3/1989 | Elliott |
| 4,846,153 A | 7/1989 | Berci |
| 4,877,016 A | 10/1989 | Kantor et al. |
| 4,884,133 A | 11/1989 | Kanno et al. |
| 4,998,972 A | 3/1991 | Chin et al. |
| 5,005,573 A | 4/1991 | Buchanan |
| 5,065,755 A | 11/1991 | Klafta |
| 5,179,938 A | 1/1993 | Lonky |
| 5,193,544 A | 3/1993 | Jaffe |
| 5,207,213 A | 5/1993 | Auhll et al. |
| 5,241,170 A | 8/1993 | Field et al. |
| 5,241,956 A | 9/1993 | Brain |
| 5,249,571 A | 10/1993 | Brain |
| 5,282,464 A | 2/1994 | Brain |
| 5,285,778 A | 2/1994 | Mackin |
| 5,287,848 A | 2/1994 | Cubb et al. |
| 5,297,547 A | 3/1994 | Brain |
| 5,305,743 A | 4/1994 | Brain |
| 5,308,323 A | 5/1994 | Sogawa et al. |
| 5,329,938 A | 7/1994 | Lonky |
| 5,329,940 A | 7/1994 | Adair |
| 5,348,690 A | 9/1994 | Cohen et al. |
| 5,355,879 A | 10/1994 | Brain |
| 5,363,838 A | 11/1994 | George |
| 5,373,317 A | 12/1994 | Salvati et al. |
| 5,400,771 A | 3/1995 | Pirak et al. |
| 5,457,613 A | 10/1995 | Vandenbelt et al. |
| 5,488,544 A | 1/1996 | Ladyjensky |
| 5,499,625 A | 3/1996 | Frass et al. |
| 5,518,502 A | 5/1996 | Kaplan et al. |
| 5,527,261 A | 6/1996 | Monroe et al. |
| 5,552,968 A | 9/1996 | Ladyjensky |
| 5,569,300 A | 10/1996 | Redmon |
| 5,580,147 A | 12/1996 | Salerno |
| 5,607,386 A | 3/1997 | Flam |
| 5,622,182 A | 4/1997 | Jaffe |
| 5,665,052 A | 9/1997 | Bullard |
| 5,666,222 A | 9/1997 | Ning |
| 5,676,635 A | 10/1997 | Levin |
| 5,702,351 A | 12/1997 | Bar-Or et al. |
| 5,716,329 A | 2/1998 | Dieter |
| 5,718,666 A | 2/1998 | Alarcon |
| 5,725,476 A | 3/1998 | Yasui et al. |
| 5,735,792 A | 4/1998 | Vanden et al. |
| 5,775,322 A | 7/1998 | Silverstein et al. |
| 5,792,053 A | 8/1998 | Skladnev et al. |
| 5,800,344 A | 9/1998 | Wood et al. |
| 5,803,898 A | 9/1998 | Bashour |
| 5,819,727 A | 10/1998 | Linder |
| 5,827,178 A | 10/1998 | Berall |
| 5,873,814 A | 2/1999 | Adair |
| 5,873,818 A | 2/1999 | Rothfels |
| 5,879,304 A | 3/1999 | Shuchman et al. |
| 5,888,195 A | 3/1999 | Schneider |
| 5,888,196 A | 3/1999 | Bonutti |
| 5,891,013 A | 4/1999 | Thompson |
| 5,904,648 A | 5/1999 | Arndt et al. |
| 5,908,294 A | 6/1999 | Schick et al. |
| 5,913,816 A | 6/1999 | Sanders et al. |
| 5,941,816 A | 8/1999 | Barthel et al. |
| 5,944,654 A | 8/1999 | Crawford |
| 6,004,265 A | 12/1999 | Hsu et al. |
| 6,024,697 A | 2/2000 | Pisarik |
| 6,050,713 A | 4/2000 | O'Donnell et al. |
| 6,067,985 A | 5/2000 | Islava |
| 6,079,409 A | 6/2000 | Brain |
| 6,091,453 A | 7/2000 | Coan et al. |
| 6,115,523 A | 9/2000 | Gravenstein et al. |
| 6,126,592 A | 10/2000 | Proch et al. |
| 6,142,144 A | 11/2000 | Pacey |
| 6,142,935 A | 11/2000 | Flom et al. |
| 6,161,537 A | 12/2000 | Gravenstein et al. |
| 6,164,277 A | 12/2000 | Merideth |
| 6,176,824 B1 | 1/2001 | Davis |
| 6,186,944 B1 | 2/2001 | Tsai |
| 6,189,533 B1 | 2/2001 | Simon et al. |
| 6,228,025 B1 | 5/2001 | Hipps et al. |
| 6,248,060 B1 | 6/2001 | Buess et al. |
| 6,260,994 B1 | 7/2001 | Matsumoto et al. |

(56) References Cited

U.S. PATENT DOCUMENTS

| | | |
|---|---|---|
| 6,266,547 B1 | 7/2001 | Walker et al. |
| 6,318,887 B1 | 11/2001 | Matsumoto |
| 6,322,498 B1 | 11/2001 | Gravenstein et al. |
| 6,331,156 B1 | 12/2001 | Haefele et al. |
| 6,419,262 B1 | 7/2002 | Fendt et al. |
| 6,419,626 B1 | 7/2002 | Yoon |
| 6,432,042 B1 | 8/2002 | Bashour |
| 6,447,446 B1 | 9/2002 | Smith et al. |
| 6,449,006 B1 | 9/2002 | Shipp |
| 6,458,076 B1 | 10/2002 | Pruitt |
| 6,478,730 B1 | 11/2002 | Bala et al. |
| 6,533,722 B2 | 3/2003 | Nakashima |
| 6,543,447 B2 | 4/2003 | Pacey |
| 6,551,240 B2 | 4/2003 | Henzler |
| 6,616,600 B2 | 9/2003 | Pauker |
| 6,628,335 B1 | 9/2003 | Numazaki et al. |
| 6,648,816 B2 | 11/2003 | Irion et al. |
| 6,655,377 B2 | 12/2003 | Pacey |
| 6,692,431 B2 | 2/2004 | Kazakevich |
| 6,712,760 B2 | 3/2004 | Sano et al. |
| 6,730,019 B2 | 5/2004 | Irion |
| 6,741,286 B2 | 5/2004 | Meek et al. |
| 6,796,939 B1 | 9/2004 | Hirata et al. |
| 6,847,394 B1 | 1/2005 | Hansen et al. |
| 6,923,176 B2 | 8/2005 | Ranzinger |
| 6,929,600 B2 | 8/2005 | Hill |
| 7,013,899 B2 | 3/2006 | Alfery et al. |
| 7,052,456 B2 | 5/2006 | Simon |
| 7,057,639 B2 | 6/2006 | Spoonhower et al. |
| 7,128,071 B2 | 10/2006 | Brain |
| 7,159,590 B2 | 1/2007 | Rife |
| 7,297,105 B2 | 11/2007 | Mackin |
| 7,384,308 B2 | 6/2008 | Boehnlein et al. |
| 7,458,375 B2 | 12/2008 | Schwartz et al. |
| 7,530,946 B2 | 5/2009 | Hartwick |
| 7,584,534 B2 | 9/2009 | Pease et al. |
| 7,658,708 B2 | 2/2010 | Schwartz et al. |
| 7,758,495 B2 | 7/2010 | Pease et al. |
| 7,862,173 B1 | 1/2011 | Ellman |
| 7,878,973 B2 | 2/2011 | Yee et al. |
| 7,938,119 B2 | 5/2011 | Chen et al. |
| 7,942,813 B2 | 5/2011 | Mackin |
| 7,946,981 B1 | 5/2011 | Cubb |
| 7,976,459 B2 | 7/2011 | Laser |
| 8,038,606 B2 | 10/2011 | Otawara |
| 8,042,545 B2 | 10/2011 | Schwartz et al. |
| 8,226,571 B2 | 7/2012 | Landesberg et al. |
| 8,231,524 B2 | 7/2012 | Schwartz et al. |
| 8,413,658 B2 | 4/2013 | Williams |
| 8,458,844 B2 | 6/2013 | Vazales et al. |
| 8,473,033 B2 | 6/2013 | Wood et al. |
| 8,475,360 B2 * | 7/2013 | Brown ............... A61B 1/00082 600/107 |
| 8,479,739 B2 | 7/2013 | Hirsh |
| 8,534,287 B2 | 9/2013 | Vazales et al. |
| 8,584,678 B2 | 11/2013 | Pol |
| 8,696,548 B2 | 4/2014 | Gilboa |
| 8,696,685 B2 | 4/2014 | Gilboa |
| 8,790,270 B2 | 7/2014 | Landesberg et al. |
| 8,863,746 B2 | 10/2014 | Totz |
| 8,887,730 B2 | 11/2014 | Wood et al. |
| 8,932,207 B2 | 1/2015 | Greenburg et al. |
| 8,978,657 B2 | 3/2015 | Sandmore et al. |
| 8,998,798 B2 | 4/2015 | Hayman et al. |
| 9,055,881 B2 | 6/2015 | Gilboa et al. |
| 9,155,854 B2 | 10/2015 | Hayman et al. |
| 9,204,794 B2 | 12/2015 | Lisogurski et al. |
| 9,211,060 B2 | 12/2015 | Waldron et al. |
| 9,242,058 B2 | 1/2016 | Hayman et al. |
| 9,271,803 B2 | 3/2016 | Averbuch et al. |
| 9,283,342 B1 | 3/2016 | Gardner |
| 9,332,891 B2 | 5/2016 | Vazales et al. |
| 9,357,905 B2 | 6/2016 | Molnar et al. |
| 9,415,179 B2 | 8/2016 | Molnar |
| 9,572,946 B2 | 2/2017 | Chun |
| 9,579,012 B2 | 2/2017 | Vazales et al. |
| 9,603,515 B2 | 3/2017 | Zocca et al. |
| 9,662,466 B2 | 5/2017 | Gunday et al. |
| 9,750,913 B2 | 9/2017 | Schwartz et al. |
| 9,788,755 B2 | 10/2017 | Hayman et al. |
| 9,801,535 B2 | 10/2017 | Turnbull |
| 9,820,642 B2 | 11/2017 | Law et al. |
| 9,826,892 B2 | 11/2017 | Dresher et al. |
| 9,854,962 B2 | 1/2018 | Mcgrail et al. |
| 9,855,111 B2 | 1/2018 | Vazales et al. |
| 9,888,832 B2 | 2/2018 | Schwartz et al. |
| 9,907,624 B2 | 3/2018 | Vazales et al. |
| 2001/0023312 A1 | 9/2001 | Pacey |
| 2001/0028227 A1 | 10/2001 | Lys et al. |
| 2002/0007110 A1 | 1/2002 | Irion |
| 2002/0045801 A1 | 4/2002 | Niida et al. |
| 2002/0062062 A1 | 5/2002 | Belson et al. |
| 2002/0072680 A1 | 6/2002 | Schock et al. |
| 2002/0076280 A1 | 6/2002 | Semotiuk et al. |
| 2002/0077527 A1 | 6/2002 | Aydelotte |
| 2002/0108610 A1 | 8/2002 | Christopher |
| 2002/0120181 A1 | 8/2002 | Irion |
| 2002/0162557 A1 | 11/2002 | Simon et al. |
| 2002/0193664 A1 | 12/2002 | Ross et al. |
| 2003/0011538 A1 | 1/2003 | Lys et al. |
| 2003/0018237 A1 | 1/2003 | Okada |
| 2003/0028078 A1 | 2/2003 | Glukhovsky |
| 2003/0030745 A1 | 2/2003 | Meek et al. |
| 2003/0035048 A1 | 2/2003 | Shipp |
| 2003/0042493 A1 | 3/2003 | Kazakevich |
| 2003/0050534 A1 | 3/2003 | Kazakevich |
| 2003/0051733 A1 | 3/2003 | Kotmel et al. |
| 2003/0078476 A1 | 4/2003 | Hill |
| 2004/0044269 A1 | 3/2004 | Shibata |
| 2004/0143167 A1 | 7/2004 | Branch et al. |
| 2004/0210114 A1 | 10/2004 | Simon |
| 2005/0039754 A1 | 2/2005 | Simon |
| 2005/0065496 A1 | 3/2005 | Simon et al. |
| 2005/0090712 A1 | 4/2005 | Cubb |
| 2007/0215162 A1 | 9/2007 | Glassenberg et al. |
| 2007/0293726 A1 | 12/2007 | Goldfarb et al. |
| 2008/0146879 A1 | 6/2008 | Pacey |
| 2008/0188715 A1 | 8/2008 | Fujimoto |
| 2008/0200764 A1 | 8/2008 | Okada |
| 2009/0227998 A1 | 9/2009 | Aljuri et al. |
| 2009/0253964 A1 | 10/2009 | Miyamoto |
| 2010/0113916 A1 | 5/2010 | Kumar |
| 2010/0249639 A1 | 9/2010 | Bhatt |
| 2011/0197888 A1 | 8/2011 | Deutsch et al. |
| 2011/0282148 A1 | 11/2011 | Kase et al. |
| 2011/0313347 A1 | 12/2011 | Zocca et al. |
| 2011/0315147 A1 | 12/2011 | Wood et al. |
| 2012/0041534 A1 | 2/2012 | Clerc et al. |
| 2012/0065469 A1 | 3/2012 | Allyn et al. |
| 2012/0172664 A1 | 7/2012 | Hayman et al. |
| 2012/0172665 A1 | 7/2012 | Allyn et al. |
| 2012/0197086 A1 | 8/2012 | Morris et al. |
| 2012/0226100 A1 | 9/2012 | Greenburg et al. |
| 2012/0259173 A1 | 10/2012 | Waldron et al. |
| 2012/0302833 A1 | 11/2012 | Hayman et al. |
| 2013/0158351 A1 | 6/2013 | Daher et al. |
| 2013/0269703 A1 | 10/2013 | Wood et al. |
| 2013/0303849 A1 | 11/2013 | Allyn et al. |
| 2013/0317339 A1 | 11/2013 | Waldstreicher et al. |
| 2013/0324798 A1 | 12/2013 | Molnar et al. |
| 2014/0024893 A1 | 1/2014 | Dorsey et al. |
| 2014/0024895 A1 | 1/2014 | Allyn |
| 2014/0031622 A1 | 1/2014 | Daher |
| 2014/0033455 A1 | 2/2014 | Vazales et al. |
| 2014/0046142 A1 | 2/2014 | Gavriely |
| 2014/0094651 A1 | 4/2014 | Allyn et al. |
| 2014/0094652 A1 | 4/2014 | Lewis et al. |
| 2014/0094653 A1 | 4/2014 | Lewis et al. |
| 2014/0128672 A1 | 5/2014 | Daher et al. |
| 2014/0150782 A1 | 6/2014 | Vazales et al. |
| 2014/0221921 A1 | 8/2014 | Gilboa |
| 2014/0309494 A1 | 10/2014 | Molnar |
| 2015/0099927 A1 | 4/2015 | Sadoughi |
| 2015/0126808 A1 | 5/2015 | Roze |

(56) References Cited

U.S. PATENT DOCUMENTS

| | | |
|---|---|---|
| 2015/0133741 A1 | 5/2015 | Gill |
| 2015/0174352 A1 | 6/2015 | Hayman et al. |
| 2015/0190044 A1 | 7/2015 | Livnat |
| 2015/0223668 A1 | 8/2015 | Gilboa et al. |
| 2015/0305596 A1 | 10/2015 | Oskin et al. |
| 2015/0305650 A1 | 10/2015 | Hunter et al. |
| 2016/0000303 A1 | 1/2016 | Klein et al. |
| 2016/0030693 A1 | 2/2016 | Nakatate et al. |
| 2016/0038008 A1 | 2/2016 | Molnar |
| 2016/0038014 A1 | 2/2016 | Molnar |
| 2016/0051221 A1 | 2/2016 | Dickhans et al. |
| 2016/0101253 A1 | 4/2016 | Alahmadi |
| 2016/0106308 A1 | 4/2016 | Field |
| 2016/0157708 A1 | 6/2016 | Daher et al. |
| 2016/0183777 A1 | 6/2016 | Daher et al. |
| 2016/0206189 A1 | 7/2016 | Nearman et al. |
| 2016/0227991 A1 | 8/2016 | Hayut et al. |
| 2016/0256646 A1 | 9/2016 | Vazales |
| 2016/0287825 A1 | 10/2016 | Daher et al. |
| 2017/0119494 A1 | 5/2017 | Vazales et al. |

FOREIGN PATENT DOCUMENTS

| | | |
|---|---|---|
| DE | 29805624 U1 | 6/1998 |
| EP | 0712601 A1 | 5/1996 |
| GB | 2357856 A | 7/2001 |
| JP | 03-258268 A | 11/1991 |
| JP | 06-022902 A | 2/1994 |
| JP | 06-217933 A | 8/1994 |
| JP | 08-117184 A | 5/1996 |
| JP | 08-126603 A | 5/1996 |
| JP | 2001-501843 A | 2/2001 |
| JP | 2001-128925 A | 5/2001 |
| JP | 2002-508982 A | 3/2002 |
| JP | 2002-514947 A | 5/2002 |
| JP | 2009-505721 A | 2/2009 |
| JP | 2011-010685 A | 1/2011 |
| WO | 94/28784 A1 | 12/1994 |
| WO | 97/29679 A2 | 8/1997 |
| WO | 98/14112 A2 | 4/1998 |
| WO | 99/35960 A1 | 7/1999 |
| WO | 99/45990 A1 | 9/1999 |
| WO | 00/54655 A1 | 9/2000 |
| WO | 01/54565 A2 | 8/2001 |
| WO | 01/56458 A1 | 8/2001 |
| WO | 02/56951 A1 | 6/2002 |
| WO | 02/85194 A1 | 10/2002 |
| WO | 03/75979 A2 | 9/2003 |
| WO | 2003/101516 A1 | 12/2003 |
| WO | 2004/030527 A1 | 4/2004 |
| WO | 2004/093791 A2 | 11/2004 |
| WO | 2008/103448 A1 | 8/2008 |
| WO | 2010/011781 A2 | 1/2010 |
| WO | 2012/091859 A1 | 7/2012 |
| WO | 2016/004302 A1 | 1/2016 |

\* cited by examiner

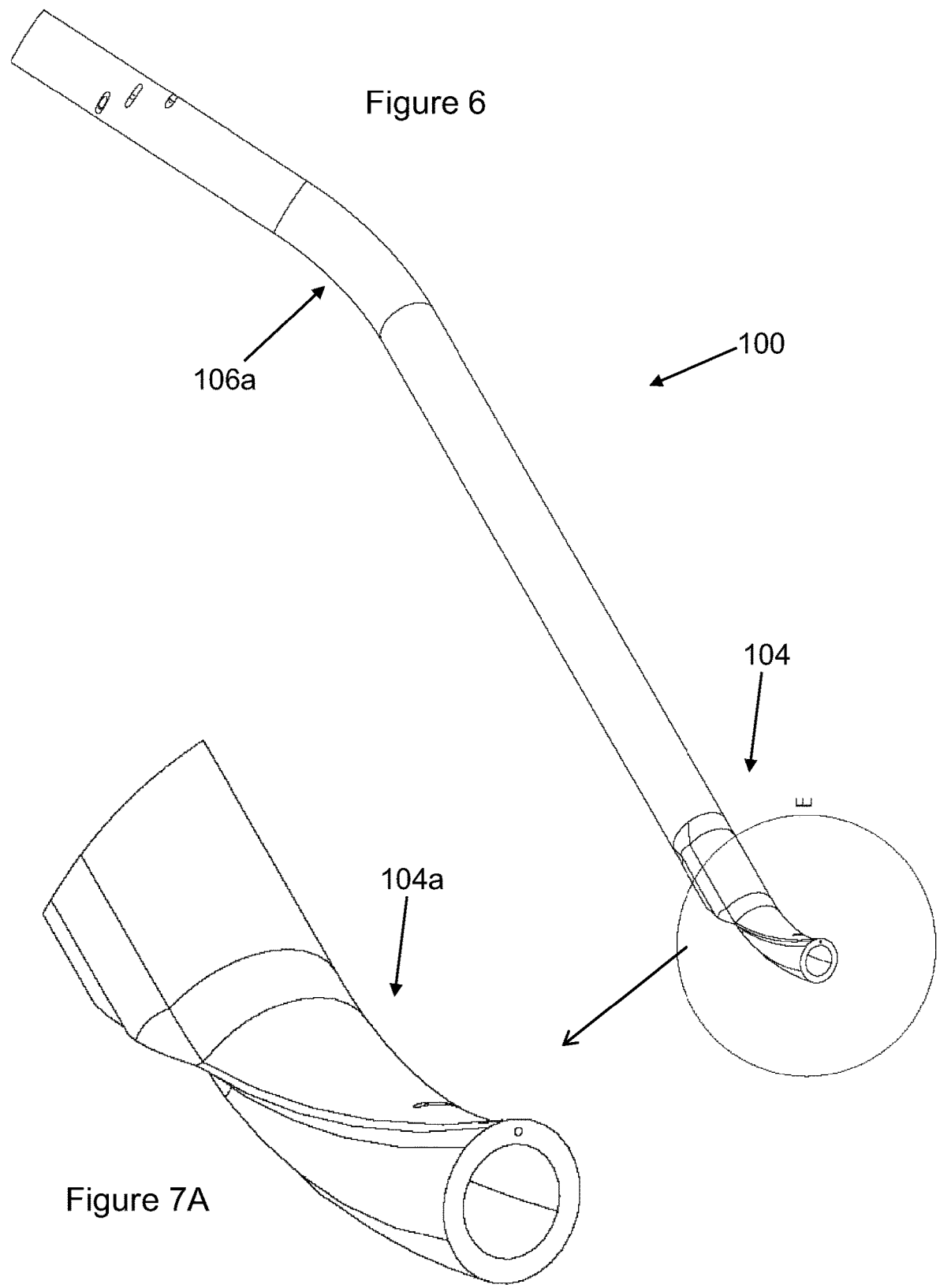

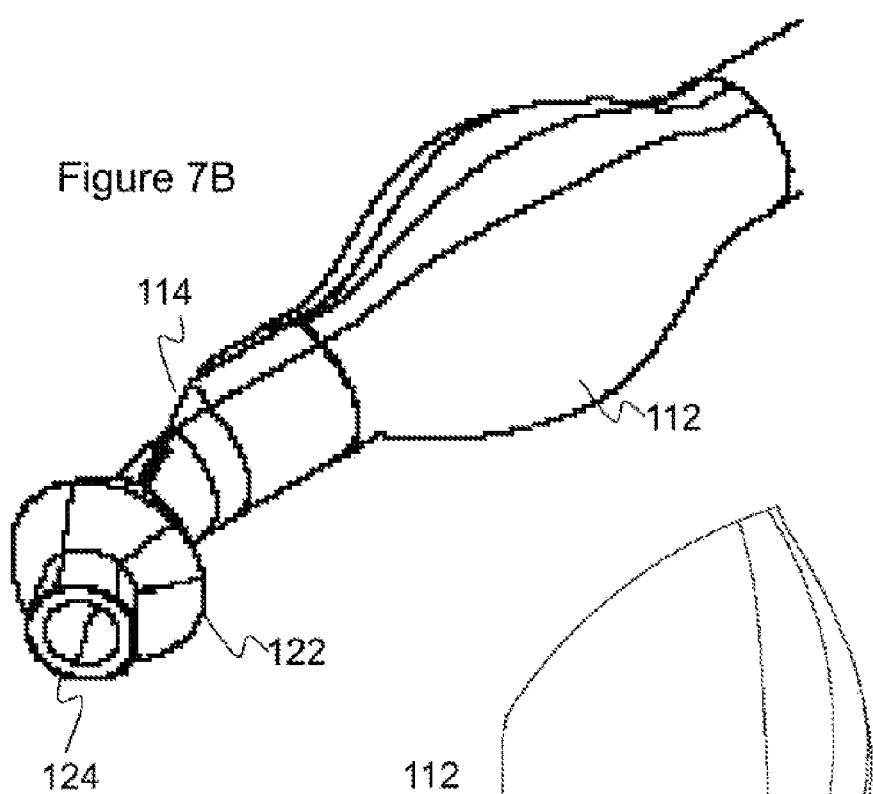
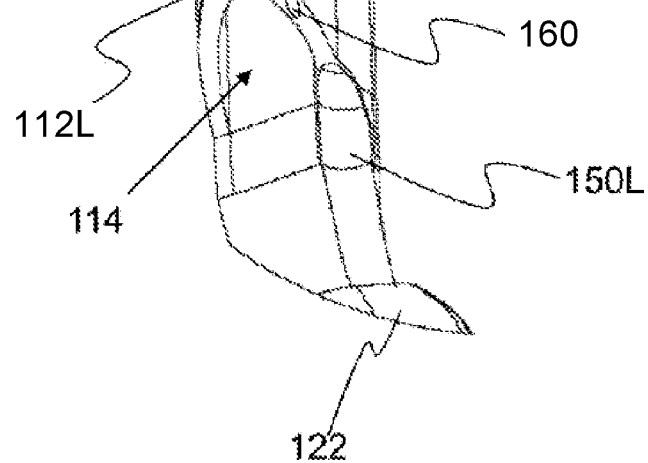

ENDOBRONCHIAL TUBE WITH INTEGRATED IMAGE SENSOR

CROSS-REFERENCE TO RELATED APPLICATIONS

This application is a Continuation of U.S. patent application Ser. No. 14/967,048, filed on Dec. 11, 2015 and issued as U.S. Pat. No. 10,245,402 on Apr. 2, 2019, which is a Continuation of U.S. patent application Ser. No. 13/819,743, filed on Feb. 28, 2013, which is a National Stage Entry of International Application No. PCT/IB2012/052077, filed on Apr. 26, 2012, which claims the benefit of U.S. Provisional Application No. 61/506,210, filed on Jul. 11, 2011. The present application is related to U.S. patent application Ser. No. 15/042,163, filed on Feb. 12, 2016, which is a continuation-in-part of U.S. patent application Ser. No. 13/737,944, filed on Apr. 26, 2012, which is a National Stage Entry of the aforementioned International Application No. PCT/IB2012/052077. The present application is also related to U.S. patent application Ser. No. 14/151,846, filed on Jan. 10, 2014 and issued as U.S. Pat. No. 10,245,402 on Dec. 11, 2018, which is a continuation-in-part of the aforementioned U.S. patent application Ser. No. 13/737,944.

FIELD OF THE INVENTION

The present invention relates to upper airway tubes and in particular, to an endobronchial tube with an integrated image sensor and light source.

BACKGROUND OF THE INVENTION

Respiratory tubes for example endobronchial tubes, endotracheal tubes, tracheostomy tubes are used to ventilate at least a portion of the respiratory system or lungs of a subject. Such respiratory tubes may be inserted in a number of ways via a non-invasive approach through an orifice or cavity such as the oral or nasal cavity. Alternatively such tubes may be introduced to a body via a minimally invasive external incision creating a port for tube insertion for example through the trachea in a tracheotomy procedure.

Such respiratory tubes may be provided as double lumen tubes, or single lumen tubes for selectively ventilating a portion of the respiratory system. For example endobronchial tubes, whether, double lumen tubes or a single lumen tube may be utilized for one-lung ventilation procedures or for selective lung ventilation of the left or right bronchi, during one-lung ventilation procedures.

In order to perform one-lung ventilation procedures without complications, the position of the respiratory tube placed within either the left or right bronchi and the trachea must be closely monitored or at least confirmed prior to initiating a procedure. Various technologies are available to confirm the tube's placement, for example capnograph, auscultation, bronchoscope and x-ray.

However these procedures take time, technique and skill to perform and therefore it is not feasible to continuously monitor the tube's placement. In particularly when the subject is moved during a procedure the tube's location may change leading to potentially dangerous displacement of the tube possibly suffocating the subject or inappropriate ventilation of the patient, for example not ventilating the correct portion of the respiratory system.

Verification by means of a bronchoscope is currently the gold standard, but none of the mentioned confirmation techniques provide continuous monitoring of the carina or provide for correct tube positioning. Furthermore, drawbacks with respect to the design and sensitivity of the bronchoscope, render its cleaning process elaborate and often inefficient and costly process, that may lead to cross infection between subjects.

SUMMARY OF THE INVENTION

There is an unmet need for, and it would be highly useful to have an endobronchial tube capable of continuously and seamlessly inspect the location and implantation of the endobronchial tube relative to the Tracheal Carina.

The present invention overcomes the deficiencies of the background by providing an endobronchial tube having an integrated image sensor and corresponding light source.

A preferred embodiment of the present invention provides for a respiratory tube, and an endobronchial tube, designed for oral or nasal insertion via the trachea and into a lung to maintain airway patency and/or deliver anesthetic, inhalation agent or other medical gases, and secure ventilation.

Most preferably the endobronchial tube of the present invention may be made of medical grade materials for example including but not limited to plastic, rubber, polymers or silicone or the like materials as is known in the art.

Most preferably the endobronchial tube of the present invention provides for continuous monitoring of the Tracheal Carina (herein "TC"), allowing a user, physician, nurse, or caregiver to verify the correct placement of the endobronchial tube Most preferably the endobronchial tube includes an integrated image sensor, optionally and preferably in the form of CCD or CMOS camera provided for visualizing the carina to confirm the correct placement of the tube within the trachea and bronchi, assuring correct ventilation during procedures for example including but not limited to one lung ventilation.

Most preferably the integrated camera and light source provide continuous verification of the correct placement of the endobronchial tube. The continuous placement verification allows a caregiver the opportunity to detect any dangerous situation, for example cuff dislodgement, providing sufficient time to react to the situation as is necessary. Moreover blood and secretion accumulation or any other unexpected incidents during surgery, which might cause risk to the patient, may be observed.

A preferred embodiment of the present invention provides for an endobronchial tube with an integrated image sensor, for example including but not limited to CCD or CMOS camera, with a corresponding light source, for example including but not limited to a Light Emitting Diode ('LED') while optimizing the lumen patency for both adequate airflow performance through the tube. Most preferably the image sensor and corresponding light source are provided in a dedicated lumen along the length of the endobronchial tube. Most preferably the image sensor is further provided with a cleaning nozzle to ensure an open field of view distal to the image sensor. Most preferably the length of the dedicated image sensor lumen is provided paralleled with the length of the tracheal lumen, therein both tracheal lumen and image sensor lumen are of essentially the same length. Optionally the length of the dedicated image sensor lumen may be provided according to the length of the bronchial lumen.

Optionally the endobronchial tube may be provided with two dedicated image sensor lumen. Optionally a first dedicated image sensor lumen is provided according to the length of the tracheal lumen and a second dedicated image sensor lumen is provided according to the length of the bronchial lumen.

A preferred embodiment of the present invention provides for an endobronchial tube with an integrated image sensor and light source provide a continuously and unobstructed view and illumination of the carina, left bronchi, right bronchi, bronchial cuff and bronchial bifurcations, within a single field of view.

An optional embodiment of the present invention provides for utilizing at least one or more bronchial cuff. Optionally at least two or more bronchial cuffs may be utilized to provide adequate sealing of the bronchi.

Optionally the bronchial cuff may be provided in varying shapes so as to better fit the bronchi for example include but is not limited to spherical, elliptical, helical, hourglass, trapezoidal, or the like.

Optionally different bronchial cuff configured and shaped according to anatomy and placement location, for example anatomy based on configuration of a cuff for left bronchi placement and for right bronchi placement.

Within the context of this application the term endobronchial tube may be used interchangeably with any one of Tracheobronchial tube, double lumen tube, double lumen endobronchial tube, double lumen endotracheal tube, to collectively refer to a tube and/or catheter utilized for selectively ventilating a subject via both lungs, one of the lungs or a portion of one or both of the lungs.

An endobronchial tube comprising at least two lumen of different lengths for selectively associating with a patient about at least two locations relative to the Tracheal Carina, the tube comprising:

a. a first lumen having an open distal end that associates proximally to the Carina within the Trachea, with a first inflatable cuff;

b. a second lumen having an open distal end that extends distally, past the Carina and associates within one of the Left Bronchial branch and Right Bronchial branch with a second inflatable cuff;

c. a dedicated image sensor lumen spanning the length of said first lumen, the dedicated image sensor lumen comprising an image sensor and illumination source disposed adjacent to the distal end of said first lumen, and configured to provide an image of the Tracheal bifurcation of the Tracheal Carina, the openings of the Left Bronchial branch, and the opening Right Bronchial branch; and d. at least one dedicated cleaning lumen disposed parallel with said dedicated image sensor lumen along the length of said endobronchial tube and wherein said cleaning lumen is configured to forms a cleaning nozzle at the distal end, wherein said cleaning nozzle is directed toward said image sensor lumen at its distal end.

Optionally, said cleaning nozzle is provided with a diameter from 0.1 mm to 2.0 mm.

Optionally, said cleaning nozzle is provided with a diameter of 0.6 mm.

Optionally, said cleaning lumen is provided with two or more cleaning nozzles about either side of said image sensor.

Optionally, said two or more cleaning nozzles cooperate with one another.

Optionally, said cleaning lumen provides for suctioning or flushing the image sensor field of view.

Optionally, said dedicated image sensor lumen is disposed within the wall of said tube about an anterior or posterior portion between said first and second lumen.

Optionally, the second lumen comprises a second image sensor providing an image of the Right bronchi or Left bronchi.

Optionally the image sensor may be a CCD image sensor or CMOS image sensor.

Optionally, the first lumen further comprises a light source disposed proximal to the distal end of said first lumen and adjacent to the image sensor.

Optionally, the light source may be selected from the group consisting of a LED, optical fiber, waveguide, light guide, and any combination thereof.

Optionally the image sensor may be disposed within a dedicated channel embedded within a wall of the first lumen.

Most preferably the image sensor may be associated with an auxiliary device for example including but not limited to a display and power supply at the proximal end of the tube most preferably about the first lumen, through a single dedicated connector for example including but not limited to a USB connector.

Optionally the endotracheal tube may be adapted for non-invasive insertion through the oral cavity or nasal cavity.

Optionally the endotracheal tube may be adapted for insertion through an external port or incision.

Optionally the endotracheal tube may be adapted for insertion through a surgical procedure or other invasive procedure.

Unless otherwise defined, all technical and scientific terms used herein have the same meaning as commonly understood by one of ordinary skill in the art to which this invention belongs. The materials, methods, and examples provided herein are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A shows the endobronchial tube within the right bronchi; and FIG. 1B shows the endobronchial tube within the left bronchi;

FIG. 6 shows a perspective view of exemplary endobronchial tube according to an optional embodiment of the present invention, depicting the curvature of the tube;

FIGS. 7A-F show varying close up views of the distal end of the endobronchial tube according to optional embodiments of the present invention;

DESCRIPTION OF THE PREFERRED EMBODIMENTS

The principles and operation of the present invention may be better understood with reference to the drawings and the accompanying description. The following reference labels listed below are used throughout the drawings to refer to objects having similar function, meaning, role, or objective.

10 Stylet;
12 Y-connector;
14 Air Balance Cap;
20 Endobronchial Tube connector assembly;
22 Endobronchial Tube connector proximal end;
24 Tracheal lumen connector portion;
26 Bronchial lumen connector portion;
28 Endobronchial Tube connector distal end;
50 endobronchial tube system;
100 endobronchial tube;
101 sectional view;
102 tube proximal end;
104 tube distal end;
104a distal curvature;
106 tube medial portion;
106a medial curvature;
108 midline partition;
110 tracheal lumen;
111 tracheal lumen connector;
112 tracheal cuff;
112n tracheal cuff notch;
114 tracheal lumen distal end;
116 tracheal lumen proximal end;
118 tracheal cuff connector;
120 bronchial lumen;
122 bronchial cuff;
124 bronchial lumen distal end;
126 bronchial lumen proximal end;
128 bronchial cuff connector;
130 injection tube connector;
150 image sensor with integrated illumination;
150C image sensor;
150I illumination source;
150L image sensor lumen;
152 image sensor notch;
154 image sensor conductor;
156 image sensor cleaning nozzle;
158 image sensor connector;
160 cleaning lumen;
TR Trachea;
TC Tracheal Carina;
BR Right Bronchi;
BL Left Bronchi.

Figure 1A:
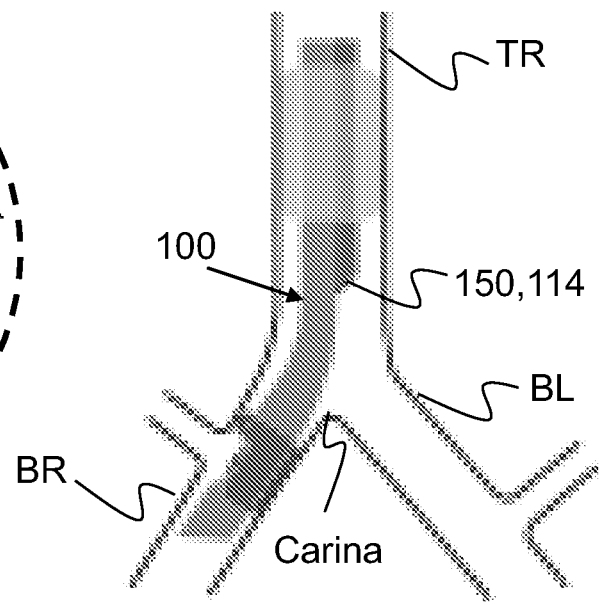
FIGS. 1A-B show schematic illustrations of an exemplary endobronchial tube according to an optional embodiment of the present invention.
Figure 1B:
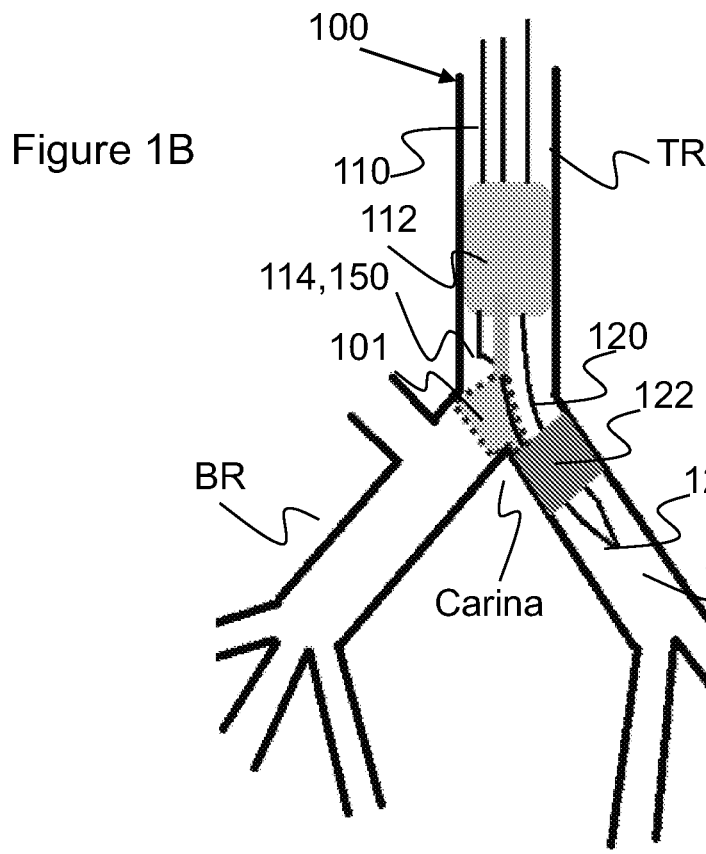

FIG. 1A shows a schematic illustration of an exemplary endobronchial tube 100 according to an optional embodiment of the present invention, placed within the right bronchi (BR). FIG. 1B shows a schematic illustration of an endobronchial tube 100 within the left bronchi (LB).

Endobronchial tube 100 is a dual lumen tube comprising a first tracheal lumen 110 and a second bronchial lumen 120. Most preferably a midline partition 108 defines the individual lumen into tracheal lumen 110 and bronchial lumen 120. Tracheal lumen 110, most preferably, ends within the trachea while the bronchial lumen 120 ends within the bronchi, left or right. Therein tracheal lumen 110 and bronchial lumen 120 are configured to have different lengths, wherein the bronchial lumen 120 extends past and/or distally to tracheal lumen 110.

Each lumen comprises an inflatable cuff respectively, tracheal cuff 112 and bronchial cuff 122. Endobronchial tube 100 is placed such that tracheal lumen 110 is placed within the Trachea by way of cuff 112 proximally, above, the tracheal carina. Most preferably the tracheal carina may be continually visualized with an image sensor and illumination source 150, also referred to as integrated image sensor 150. Optionally image sensor and illumination source 150 may be integrated within tracheal lumen 110 about its distal end 114. Optionally and most preferably image sensor and illumination source 150 may be integrated within a dedicated channel or peripheral lumen 150L, also referred to as image sensor lumen 150L, within a wall of the tracheal lumen 110. Most preferably image sensor 150C provides a cross sectional view 101, shown in FIG. 2.

Figure 2:
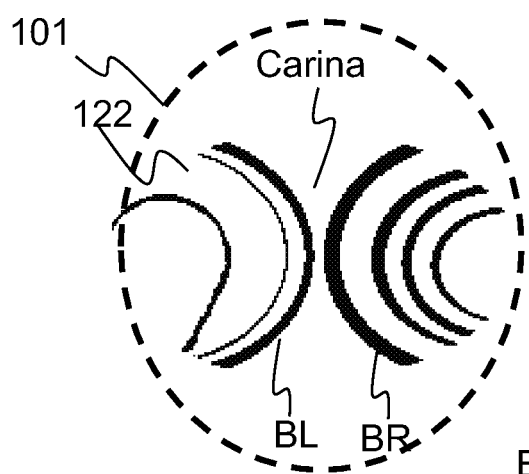
FIG. 2 shows a schematic sectional view of the Tracheal Carina as seen from the endobronchial tube according to an optional embodiment of the present invention.

Most preferably image sensor and illumination source 150 is provided in the form of at least one or more light emitting diode ('LED') 150I and image sensor 150C, for example including but not limited to a CCD or CMOS, (FIG. 9) providing a view 101 showing the status of the bronchi, FIG. 2.

FIG. 2 shows a schematic sectional view of the Tracheal Carina as seen from endobronchial tube 100, provided by image sensor and illumination source 150, allowing the visualization of bronchial cuff 122 disposed within the left bronchi BL, the patency of the left bronchi, the patency of the right bronchi, the tracheal carina, bronchial bifurcation, in a single field of view 101. Optionally a similar view may be provided with integrated image sensor 150 when endobronchial tube 100 is disposed with the right Bronchi BR as shown in FIG. 1A.

Figure 3:
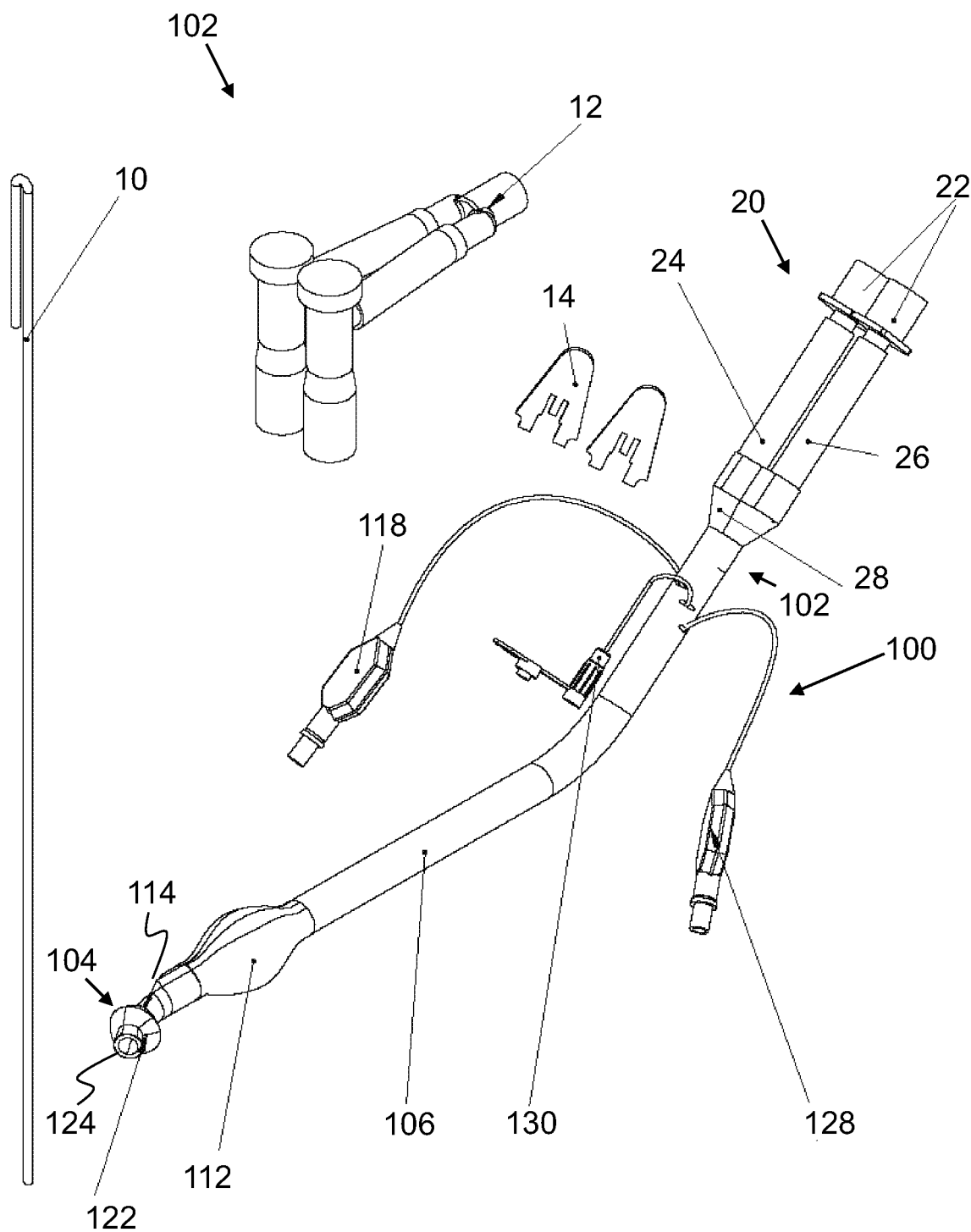
FIG. 3 shows a perspective views of an exemplary endobronchial tube according to an optional embodiment of the present invention.

FIG. 3 shows endobronchial double lumen tube system 50 comprising endobronchial tube 100 and optional various auxiliary devices that may be used in conjunction with and/or facilitate the use of endobronchial tube 100.

Optionally auxiliary devices may, for example, include but are not limited to stylet 10, Y-connector 12, air balance caps 14, and an endobronchial tube connector assembly 20, or the like adjunct device utilized facilitating the use of endobronchial tube 100 as is known in the art.

Stylet 10 most preferably is utilized to facilitate placement of endobronchial tube 100, as is known and accepted in the art.

Y-connector 12 most preferably provides for simultaneously connecting both lumens of double lumen tube 100 to a single ventilation source.

Endobronchial Tube connector assembly 20 provides for individually connecting to tracheal lumen 110 and bronchial lumen 120. Connector is assembly 20 comprises a proximal end 22, distal end 28, and respective tracheal lumen connector portion 24 and Bronchial connector portion 26.

Most preferably proximal end 22 provides for connecting and/or otherwise associating endobronchial tube 100 at proximal end 102 at about the individual lumen tracheal lumen 110 and bronchial lumen 120 to auxiliary devices for example including but not limited to ventilation sources.

Most preferably distal end 24 provides for coupling and/or otherwise associating with endobronchial tube 100.

FIG. 3 further provides a perspective view of a preferred double lumen endobronchial tube 100 comprising tracheal lumen 110 having a tracheal lumen distal end 114 and bronchial lumen 120 having a bronchial lumen distal end 124. Also shown in FIG. 3 are a tube proximal end 102, a tube medial portion 106, and a tube distal end 104 of a tube 140 (FIGS. 8A and 8B) of endobronchial tube 100, which are also the proximal end, medial portion, and distal end of endobronchial tube 100.

Endobronchial tube 100 further comprises tracheal cuff 112, shown in its expanded state, provided for securely placing and/or anchoring endobronchial tube 100 within the trachea while ventilating the lungs through tracheal lumen 110. Tracheal cuff 112 is supported by tube 140.

Tube 100 further comprises bronchial cuff 122, shown in its expanded and/or inflated state, provided for securely placing and/or anchoring endobronchial tube 100 within the bronchi, left or right. Most preferably cuff 122 provides for selectively controlling the ventilation to the bronchial arch wherein it is placed (left or right). For example ventilation to either the left or right bronchi may be completely blocked so as to allow a procedure on the respective lung (for example right) while allowing the ventilation of the other lung (for example left) via tracheal lumen 110. Broncheal cuff 122 is supported by tube 140.

Most preferably tracheal cuff 112 may be inflated and/or deflated via cuff tracheal connector 118.

Most preferably bronchial cuff 122 may be inflated and/or deflated via cuff bronchial connector 128.

Most preferably injection tube connector 130 provides an access point to a dedicated lumen about each of the tracheal lumen 110 and bronchial tube 120, preferably for delivering drugs, suctioning liquids about tracheal distal 114 and/or bronchial lumen distal end 124.

Figure 4:
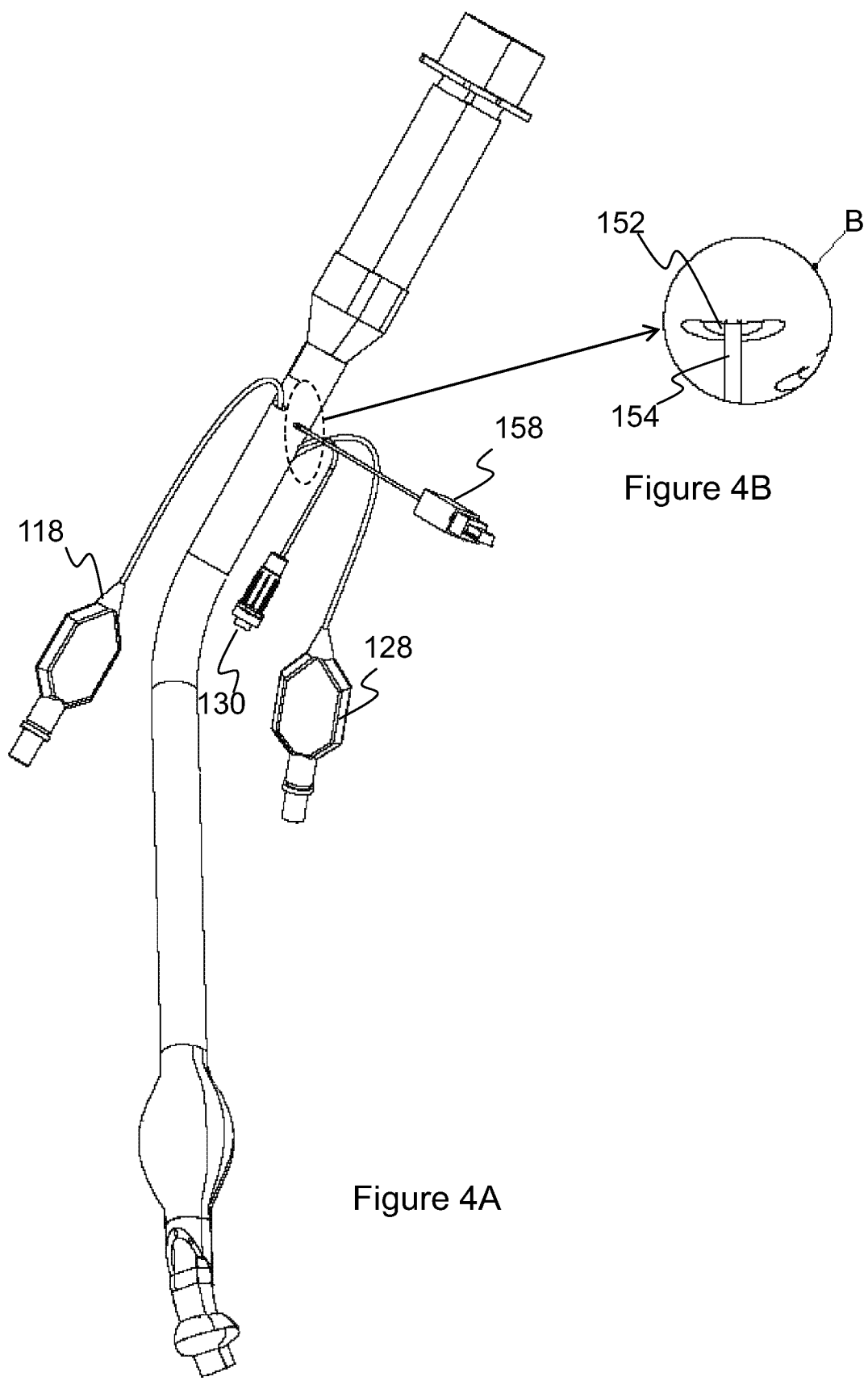
FIG. 4A shows a perspective view of an exemplary endobronchial tube according to an optional embodiment of the present invention.
FIG. 4B shows a close up view of notch exit point for the image sensor connector according to the present invention.

FIG. 4A provide a further perspective view of endobronchial tube 100, showing image sensor connector 158. Most preferably image sensor connector 158 is provided in the form of a USB connector that provides both for image and power supply to image sensor 150 disposed in a dedicated lumen near distal end 114. Optionally and preferably image sensor and illumination source 150 may be rendered function when connected to a display and power source (not shown) via connector 158.

FIG. 4B provides a close up view showing the image sensor notch 152 disposed about the proximal end of image sensor lumen 150L providing an exit point for image sensor conducting wires 154, most preferably provided for both image transfer and power supply to image sensor and illumination source 150.

Figure 5:
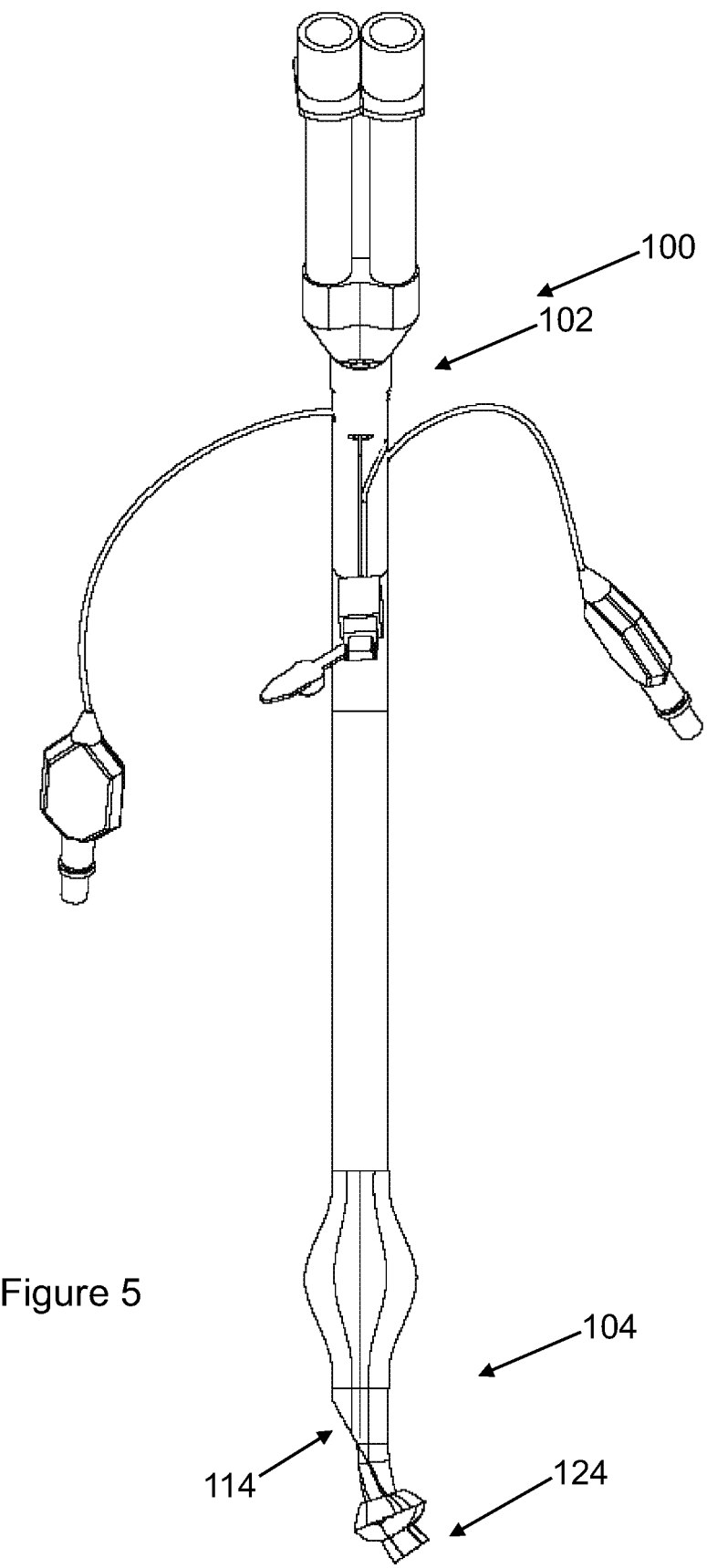
FIG. 5 shows a perspective view of exemplary endobronchial tube according to an optional embodiment of the present invention.

FIG. 5 provides a further perspective view of endobronchial tube 100 provided from a face on view showing the separation of tracheal lumen 110 and bronchial lumen 120 at distal end 104 of endobronchial tube 100.

FIG. 6 provides a further schematic illustrative depiction of endobronchial tube 100 showing a perspective view of endobronchial tube 100 with bronchial cuff 122 and tracheal cuff 112 removed. FIG. 6A shows the curvature provided at both medial section 106 and distal end 104 therein defining a medial curvature 106a and a distal curvature 104a. Curvatures 104a and 106a are provided to so that endobronchial tube 100 fits within the upper airway tract's anatomy.

Most preferably medial curvature 106a is provided for the ease of accessing and introducing tube 100 within the trachea through the oral cavity and pharynx. Most preferably, curvature 106a is provided with an angle from about 100 degrees to about 160 degrees.

Most preferably distal curvature 104a is proved for ease of accessing and introducing distal end 104 into one of the bronchi, left or right. Optionally and preferably distal curvature 104a may be specific for individual left or right endobronchial tubes. Optionally distal curvature may be configured to be from about 25 degrees to about 70 degrees. Optionally and preferably about 35 degrees as shown.

Optionally the length of endobronchial tube 100 may be provided with a length from about 200 mm to about 550 mm. Optionally and preferably the length of tube 100 may be selected in accordance with a user's anatomy.

Optionally endobronchial tube 100 may be provided with different sizes, length, diameters as known and accepted in the art. Optionally endobronchial tube 100 may be provided with a gauge from about 26 Fr to about 44 Fr, or from about, for example, the external diameter of tube 140 may be provided in varying gauges and/or sizes for example including but not limited to 28 Fr, 32 Fr, 35 Fr, 37 Fr, 39 Fr and 41 Fr, within the context of this application the units 'Fr' refer to the gauge of the tube 140 in the units French as is a common term of the art. Alternatively the gauge and or size of tube 140 may be provided in the SI units of millimeters 'mm'. Tube 140 according to the present invention may be provided with an external diameter of about 9.3 mm, 10.7 mm, 11.7 mm, 13 mm and 13.7 mm.

Optionally and preferably the length and diameter (also referred to as gauge) of tube 100 may be correlated with one another.

FIG. 7A shows a close up view of distal end 104 of endotracheal tube 100 shown in FIG. 6 providing a close up view. FIG. 7A further shows a close up view of curvature 104a showing the flaring of distal end 104 from the tracheal lumen into the side portion of bronchial lumen 120.

FIGS. 7A-E show various close up view of distal end 104 specific to curvature 104a showing the flaring and tapering of distal end 104 from the tracheal lumen into the side portion of bronchial lumen 120.

Figure 7D:
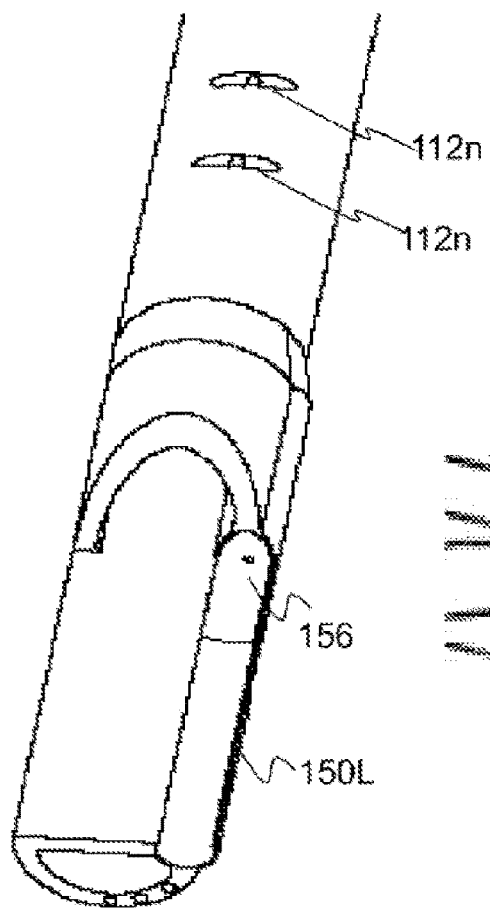
Figure 7F:
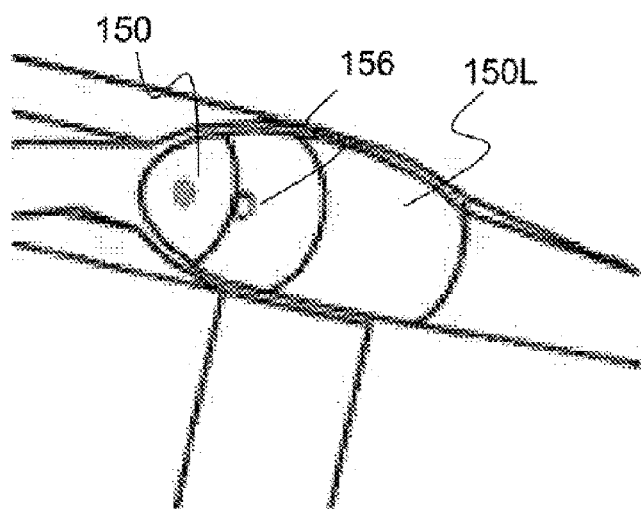
Figure 7E:
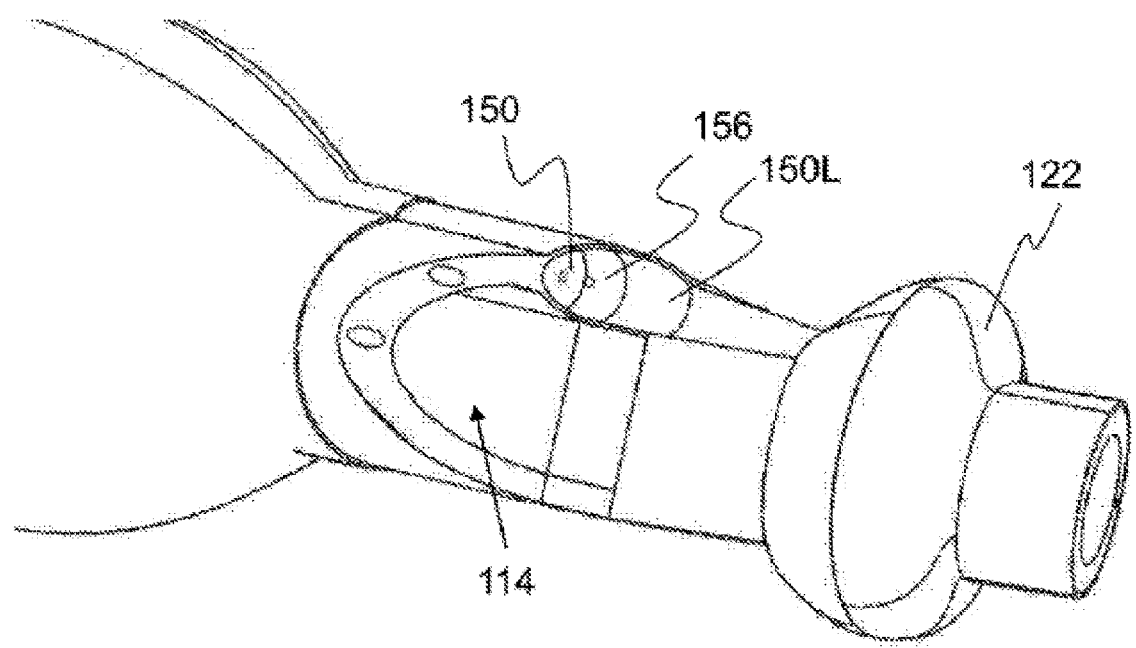

FIGS. 7D-E provide further close up views of the distal end of image sensor lumen 150L and cleaning nozzle 156, most preferably provided for cleaning image sensor. Optionally and preferably cleaning nozzle 156 is provided with an opening having a diameter from about 0.1 mm to about 2.0 mm. Optionally and preferably cleaning nozzle 156 may be provided with a diameter of about 0.6 mm.

Image sensor 150 is most preferably provided in a dedicated image sensor lumen 150L that spans the length of endobronchial tube 100. Most preferably image sensor lumen 150L is disposed between tracheal lumen 110 and bronchial lumen 120.

Most preferably distal end of image sensor lumen 150L provides for visualizing the carina and bronchial cuff 122, for example as shown in FIG. 2.

Most preferably the diameter of image sensor lumen 150L is variable along the length of endobronchial tube 100. Most preferably image sensor lumen 150 is smallest at the proximal end 102 and largest at the distal end 104. Optionally and preferably at proximal end 102 image sensor lumen 150L is configured to have an elliptical cross-section. Optionally and preferably at distal end of image sensor lumen 150L is configured to have a circular cross-section.

Most preferably alongside image sensor lumen 150L is a dedicated cleaning lumen 160 that has a distal end defining a cleaning nozzle 156, as shown, providing for cleaning integrated image sensor 150 about its distal end. Optionally and preferably cleaning nozzle 156 is provided with a curvature and/or angle so as to direct cleaning solution, fluid, gas or the like flowing fluid toward and/or away from integrated image sensor 150 and more preferably image sensor 150C. For example cleaning lumen 160 may be utilized to clear mucus or the like biological obstruction from in front of integrated image sensor 150 by flushing with a flowing fluid, for example a liquid or gas, from the proximal end of lumen 160 through to its distal end at forming cleaning nozzle 156. Optionally cleaning lumen 160 may be used to clear the viewing field of integrated image sensor 150 by applying suctioning therein suctioning in front of the field of view to keep it clean.

FIG. 7F shows a close up view of cleaning nozzle 156 as directed toward image sensor 150C about the distal end of image sensor lumen 150L. Optionally and preferably cleaning nozzle 156 is configured such that it provides for maintaining an open field of view of the Tracheal Carina for integrated image sensor 150.

Optionally and preferably the distal end of cleaning lumen 160 may be curved such that the distal end is directed toward the distal end of image sensor lumen 150L therein providing for forming at least one or more cleaning nozzle 156 that is optionally and preferably directed toward image sensor 150C, for example as shown in FIG. 7E.

Optionally endobronchial tube 100 may be provided with at least two or more cleaning lumen 160. Optionally a first cleaning lumen may be provided for flushing biological obstruction while a second cleaning lumen may be provided for suctioning biological obstructions away from the distal end 114. Optionally a plurality of cleaning lumen 160 may be disposed on opposite sides of integrated image sensor 150. Optionally a plurality of cleaning lumen 160 may be configured to cooperate with one another, for example a first lumen would flush biological obstructions toward a dsecond cleaning lumen where the obstruction is carried away by suctioning. Optionally at least two or more cleaning lumen may be utilized concertedly to either suction or flush obstructions distal to integrated image sensors 150, therein most preferably ensuring an open viewing field. Optionally a plurality of cleaning lumen may be provided with different diameters and or sizes.

Figure 8A:
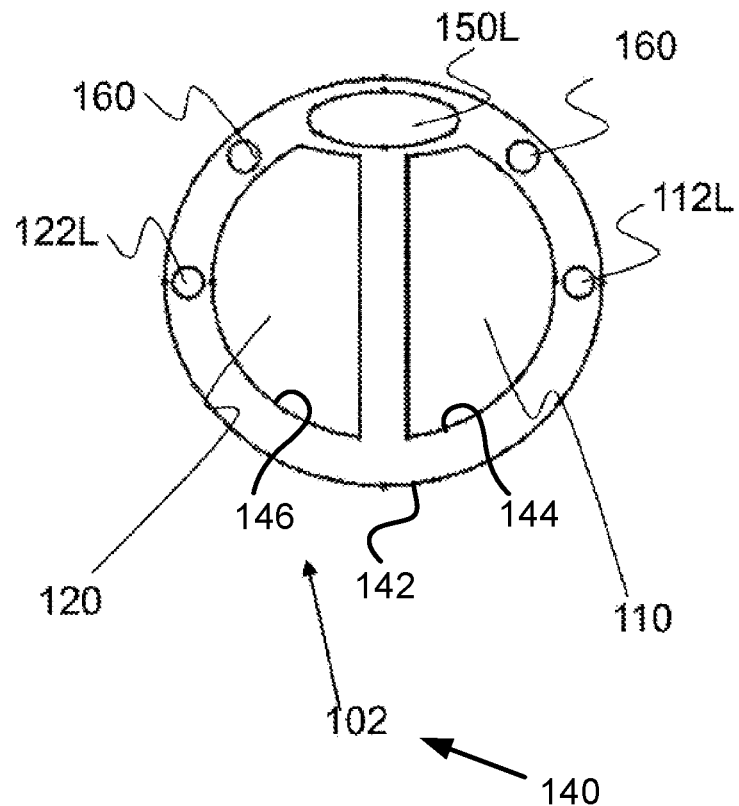
FIGS. 8A-B show cross-sectional views about different portions of the endobronchial tube according to optional embodiments of the present invention.

FIG. 8A shows a cross sectional view of tube 140 of endobronchial tube 100 about its proximal end 102 having tracheal lumen 110 and a bronchial lumen 120 defined on either side of a midline partition 108. Tube 140 comprises an exterior surface 142 and interior surfaces 144, 146 of, respectively, tracheal lumen 110 and bronchial lumen 120. Most preferably tube 140 of endobronchial tube 100 comprises a plurality of peripheral lumen disposed internally and/or within the walls of endobronchial tube 100. Most preferably a plurality of peripheral lumen may be disposed about the circumference of tube 140 and span essentially the length of tube 140, about the tracheal lumen 110 and/or bronchial lumen 120. Optionally and preferably the peripheral lumen may for example include but is not limited to a suctioning lumen, cuff inflating lumen, electronic lumen, image sensor lumen, cleaning lumen, injection tube lumen, or the like.

Most preferably endobronchial tube 100 includes a dedicated image sensor lumen 150L provided for image sensor and integrated illumination source 150. Most preferably image sensor lumen 150L provides for housing integrated image sensor 150 at its distal end (FIG. 7E-F) and housing image sensor conductors 154, for example in the form of a wire, disposed along the length of image sensor lumen 150L, and a image sensor notch 152 disposed near the proximal end of image sensor lumen 150L allowing image sensor conductors 154 and connector 158 to be disposed external to endobronchial tube 100.

Optionally and preferably image sensor lumen 150L is disposed about the anterior portion of endobronchial tube 100 about the middle of the cross-section of endobronchial tube 100. Most preferably image sensor lumen 150L is disposed anterior to partition 108. Optionally image sensor lumen 150L may be disposed about the posterior portion of endotracheal tube 100 therein posterior to partition 108.

Most preferably on both sides of image sensor lumen 150L are dedicated lumen running along the length of endobronchial tube 100 and most preferably running parallel with image sensor lumen 150L. Optionally and preferably at least one or more of lumen are provided as a dedicated cleaning lumen 160. Optionally both lumen flanking image sensor lumen 150L may be dedicated cleaning lumen 160.

Most preferably the tube wall further comprises inflation lumens 112L and 122L respectively corresponding to tracheal lumen 110 and bronchial lumen 120. Optionally and preferably lumen 112L and 122L are provided for inflating and/or deflating cuffs 112 and 122, respectively.

Figure 8B:
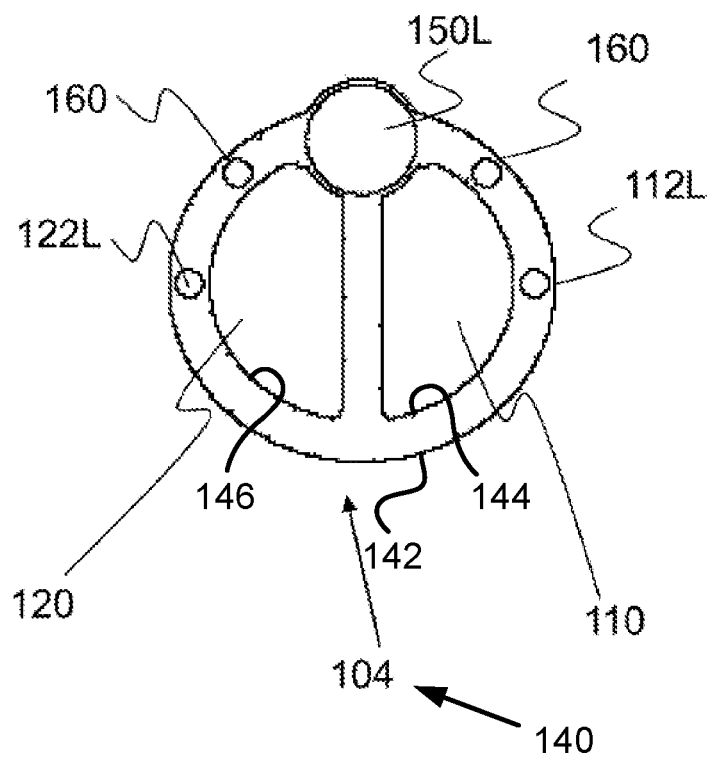

FIG. 8B shows the same image as in FIG. 8A however showing the cross-section near tracheal lumen distal end 114 of endobronchial tube 100. Most preferably at tracheal lumen distal end 114 image sensor lumen 150L is provided with a lumen having a larger radius than that provided at the proximal end 102 as shown in FIG. 8A. Most preferably endobronchial tube 100 is expanded about distal end 104 and lumen 150L to accommodate integrated image sensor 150. Optionally image sensor lumen 150 about the external surface of tube 110 is widened and/or expanded 1.5 mm to 5 mm from distal end 114 of tracheal lumen 110.

Optionally the image sensor dedicated lumen 150L is provided with an notch 150n disposed 22.5 mm from the proximal end 102 of endobronchial tube 100 and an exit notch having a diameter of about 1.5 mm.

Figure 9:
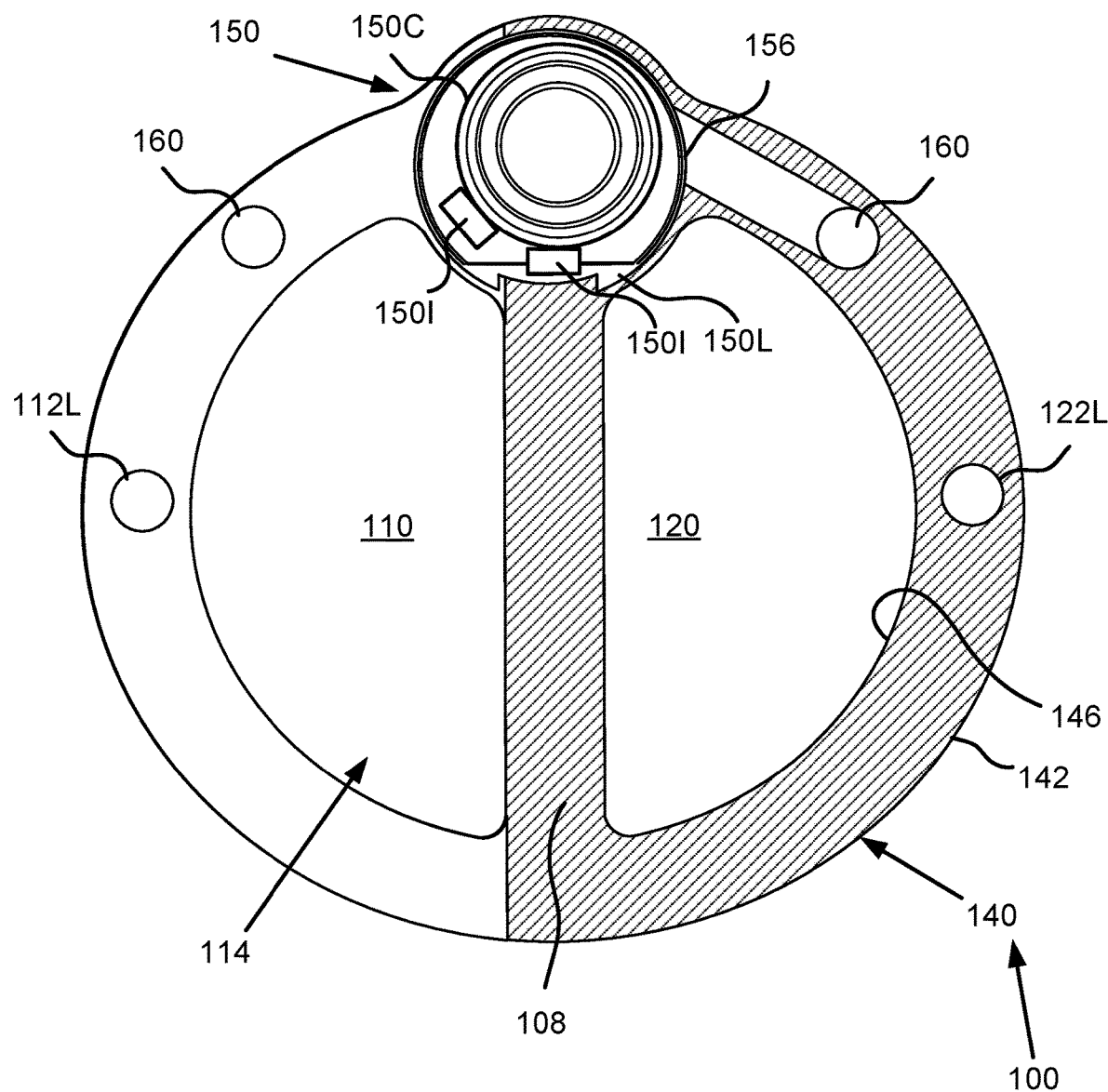
FIG. 9 shows a close up view of the image sensor with integrated light source within a dedicated lumen disposed within the wall of the endobronchial tube according to an optional embodiment of the present invention.

FIG. 9 shows a close up bottom-up view of the integrated image sensor 150 within dedicated image sensor lumen 150L disposed within the wall of endobronchial tube 100, showing image sensor 150C optionally and preferably provided in the form of a CCD or CMOS or the like, and illumination source 150I most preferably provided in the form of at least one and more preferably at least two or more LED, as shown.

While the invention has been illustrated primarily with reference to a left bronchi endobronchial tube, it will be appreciated that the present invention is not limited to a left bronchi endobronchial tube where the inventive and novel aspects equally covers a right bronchi endobronchial tube.

While the invention has been described with respect to a limited number of embodiments, it will be appreciated that many variations, modifications and other applications of the invention may be made.

What is claimed is:

1. An endobronchial tube comprising at least two lumens of different lengths for selectively associating with a patient about at least two locations relative to the Tracheal Carina, said tube comprising:
   a. a first lumen having an open distal end adapted to associate proximally to the Carina within the Trachea, with a first inflatable cuff;

b. a second lumen having an open distal end adapted to extend distally, past the Carina and associate within one of the Left Bronchial branch and Right Bronchial branch with a second inflatable cuff;
c. a dedicated image sensor lumen spanning the length of said first lumen, located within a wall of said tube between said first lumen and said second lumen, the dedicated image sensor lumen comprising an image sensor and illumination source disposed adjacent the distal end of said first lumen, and configured to provide an image of the Tracheal bifurcation of the Tracheal Carina, the openings of the Left Bronchial branch, and the opening Right Bronchial branch; and
d. at least one dedicated cleaning lumen disposed parallel with said dedicated image sensor lumen along the length of said endobronchial tube, disposed within said wall of said tube between said first lumen and said second lumen, and wherein said cleaning lumen curves at the distal end to form a cleaning nozzle, such that the distal end of said cleaning lumen is directed toward the distal end of said image sensor lumen.

2. The tube of claim 1, wherein said cleaning nozzle is provided with a diameter from 0.1 mm to 2 mm.

3. The tube of claim 2, wherein said cleaning nozzle is provided with a diameter of 0.6 mm.

4. The tube of claim 1, wherein said cleaning lumen is provided with two or more cleaning nozzles about either side of said image sensor.

5. The tube of claim 4, wherein said two or more cleaning nozzles cooperate with one another.

6. The tube of claim 1, wherein said cleaning lumen provides for suctioning or flushing the image sensor field of view.

7. The tube of claim 1, wherein said dedicated image sensor lumen is disposed within the wall of said tube about an anterior or posterior portion between said first and second lumen.

8. The endobronchial tube of claim 1, wherein said second lumen comprises a second image sensor providing an image of the Right bronchi or Left bronchi.

9. The endobronchial tube of claim 1, wherein said image sensor is a CCD image sensor or CMOS image sensor.

10. The endobronchial tube of claim 1, wherein said light source is selected from the group consisting of a LED, optical fibre, waveguide, light guide, and any combination thereof.

11. The endobronchial tube of claim 1, adapted for non-invasive insertion through the oral cavity or nasal cavity.

12. The endobronchial tube of claim 1, adapted for insertion through an external port or incision.

13. The endobronchial tube of claim 1, adapted for insertion through surgery or other invasive procedure.

* * * * *